US00PP16130P2

(12) United States Plant Patent
Brown

(10) Patent No.: US PP16,130 P2
(45) Date of Patent: Nov. 29, 2005

(54) ***PETUNIA* PLANT NAMED 'PETPO29'**

(50) Latin Name: *Petunia×hybrida*
Varietal Denomination: Petpo29

(75) Inventor: Graham Noel Brown, Pennant Hills (AU)

(73) Assignee: NuFlora International Pty. LTD., Macquarie Fields (AU)

( * ) Notice: Subject to any disclaimer, the term of this patent is extended or adjusted under 35 U.S.C. 154(b) by 38 days.

(21) Appl. No.: 10/959,829

(22) Filed: Oct. 6, 2004

(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—C. A. Whealy

(57) ABSTRACT

A distinct cultivar of *Petunia* plant named 'Petpo29', characterized by its compact and outwardly spreading plant habit; freely branching habit; and numerous flowers that are red purple in color.

1 Drawing Sheet

Botanical classification/cultivar designation: *Petunia×hybrida* cultivar Petpo29.

BACKGROUND OF THE INVENTION

The present Invention relates to a new and distinct cultivar of *Petunia* plant, botanically known as *Petunia×hybrida*, and hereinafter referred to by the cultivar name Petpo29.

The new *Petunia* is a product of a planned breeding program conducted by the Inventor in Cobbitty, New South Wales, Australia. The objective of the breeding program is to create new compact and outwardly spreading *Petunias* with numerous small flowers with attractive flower colors.

The new *Petunia* originated from a cross-pollination made by the Inventor in September, 2000 of a proprietary *Petunia* selection identified as X99.2, not patented, as the female, or seed parent, with a proprietary *Petunia* selection identified as code number X99.23a, not patented, as the male, or pollen parent. The new *Petunia* was selected as a single plant from the resulting progeny of the cross-pollination by the Inventor in October, 2001, in a controlled environment in Cobbitty, New South Wales, Australia.

Asexual reproduction of the new cultivar by terminal cuttings in a controlled environment in Cobbitty, New South Wales, Australia since October, 2001 has shown that the unique features of this new *Petunia* are stable and reproduced true to type in successive generations.

SUMMARY OF THE INVENTION

Plants of the cultivar Petpo29 have not been observed under all possible environmental conditions. The phenotype may vary somewhat with variations in environment such as temperature and light intensity without, however, any variance in genotype.

The following traits have been repeatedly observed and are determined to be the unique characteristics of 'Petpo29'. These characteristics in combination distinguish 'Petpo29' as a new and distinct *Petunia* cultivar:

1. Compact and outwardly spreading plant habit.
2. Freely branching habit.
3. Numerous red purple-colored flowers.

Plants of the new *Petunia* differ primarily from plants of the female parent in flower color as plants of the female parent selection have lavender-colored flowers. Plants of the new *Petunia* differ primarily from plants of the male parent selection in flower color as plants of the male parent selection have hot pink-colored flowers with white-colored centers.

Plants of the new *Petunia* can be compared to plants of the cultivar MP7, disclosed in U.S. Plant Pat. No. 12,819. In side-by-side comparisons conducted in Cobbitty, New South Wales, Australia, plants of the new *Petunia* differed from plants of the cultivar MP7 in the following characteristics:

1. Plants of the new *Petunia* had larger flowers than plants of the cultivar MP7.
2. Flowers of plants of the new *Petunia* were brighter in color than plants of the cultivar MP7.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia*.

The photograph at the bottom of the sheet comprises a side perspective view of a typical flowering plant of 'Petpo29' grown in a container.

The photograph at the top of the sheet comprises a close-up view of typical flowers and leaves of 'Petpo29'.

DETAILED BOTANICAL DESCRIPTION

The aforementioned photographs and following observations and measurements describe plants grown in Encinitas, Calif., in an outdoor nursery during the spring with day temperatures about 24° C., night temperatures about 19° C. and light levels about 4,000 foot-candles. Plants were grown for 21 weeks in one-gallon containers with three plants per container. Plants were pinched one time. Color references are made to The Royal Horticultural Society Colour Chart, 1995 Edition, except where general terms of ordinary dictionary significance are used.

Botanical classification: *Petunia×hybrida* cultivar Petpo29.

Parentage:

*Female parent.*—Proprietary *Petunia×hybrida* selection identified as X99.2, not patented.

*Male parent.*—Proprietary *Petunia×hybrida* selection identified as X99.23a, not patented.

Propagation:

*Type cutting.*—Terminal vegetative cuttings.

*Time to initiate roots.*—About 10 days at 22° C.

*Time to develop roots.*—About 21 days at 22° C.

*Root description.*—Fine, fibrous, white in color.

*Rooting habit.*—Freely branching, dense.

Plant description:

*Form.*—Annual flowering plant; indeterminate; compact; initially upright, then low mounding and outwardly spreading plant habit; plants eventually becoming hemispherical to spherical in shape. Viscid and glandular pubescent. Moderately vigorous.

*Branching habit.*—Freely branching with about four to five primary lateral branches per plant.

*Plant height.*—About 15 cm.

*Plant diameter, single plant.*—About 22.5 cm.

*Lateral branches.*—Length: About 12 cm. Diameter: About 2 mm. Internode length: About 8 mm. Texture: Pubescent. Color: 144B.

*Foliage description.*—Arrangement: Before flowering commences: Alternate, simple. After flowering commences: Opposite; simple. Length: About 3 cm. Width: About 1.6 cm. Shape: Elliptical. Apex: Broadly acute. Base: Attenuate. Margin: Entire. Texture, upper and lower surfaces: Slightly glandular; pubescent. Venation pattern: Pinnate. Color: Developing and fully expanded foliage, upper surface: 146A. Developing and fully expanded foliage, lower surface: 146B. Venation, upper and lower surfaces: 146B. Petiole length: About 1 cm. Petiole diameter: About 1 mm. Petiole texture, upper and lower surfaces: Slightly glandular; pubescent. Petiole color: 144A.

Flower description:

*Flower type and habit.*—Single salverform flowers; flowers face mostly upward or outward; axillary. Flowers persistent. Freely flowering, about six flowers and flower buds per lateral branch.

*Natural flowering season.*—Long day responsive; spring until frost in the autumn; flowering continuous.

*Flower longevity on the plant.*—About seven to ten days.

*Fragrance.*—Not detected.

*Flower size.*—Diameter: About 3.8 cm. Tube length: About 2.7 cm. Throat diameter, distal end: About 1.3 cm. Tube diameter, proximal end: About 3 mm.

*Flower buds* (*showing color*).—Length: About 2.6 cm. Diameter: About 7 mm. Shape: Oblong. Color: More gray than 185C.

*Corolla.*—Quantity/arrangement: Five petals; fused, funnelform. Petal length from throat: About 1.7 cm. Petal width: About 2 cm. Petal shape: Roughly spatulate or fan-shaped. Petal apex: Rounded with pointed apices. Petal margin: Entire. Petal texture: Smooth, satiny. Color: Petal, upper surface, when opening: 67A. Petal, lower surface, when opening: 75B. Petal, upper surface, fully opened: 67B; color becoming closer to 70B with development. Petal, lower surface, fully opened: 75C. Flower throat (inside): 75D. Flower tube (outside): 155D tinted with 75B. Venation, upper petal surface: 67B. Venation, lower petal surface: 194A. Venation, throat: 195A. Venation, tube: 194A.

*Sepals.*—Arrangement/appearance: Single whorl of five sepals fused at base, star-shaped. Length: About 1 cm. Width: About 2.5 mm. Shape: Strap-like; ligulate. Apex: Rounded. Margin: Entire. Texture, upper and lower surfaces: Pubescent. Color, upper surface: 146A. Color, lower surface: 146B.

*Peduncles.*—Length: About 2.2 cm. Width: About 1 mm. Angle: About 45° from the stem. Strength: Moderately strong. Texture: Pubescent. Color: 144A.

*Reproductive organs.*—Stamens: Quantity: Five per flower. Anther shape: Oval. Anther length: About 2 mm. Anther color: 160C. Pollen amount: Scarce. Pollen color: 160C. Pistils: Quantity: One per flower. Pistil length: About 1.5 cm. Style length: About 1.2 cm. Style color: 144C. Stigma shape: Oval. Stigma color: 144A. Ovary color: 144A.

*Fruit/seed.*—Fruit and seed production has not been observed.

Disease/pest resistance: Plants of the new *Petunia* have not been noted to be resistant to pathogens or pests common to *Petunia*.

Temperature tolerance: Plants of the new *Petunia* have been observed to tolerate temperatures from 4 to 34° C.

It is claimed:

1. A new and distinct cultivar of *Petunia* plant named 'Petpo29', as illustrated and described.

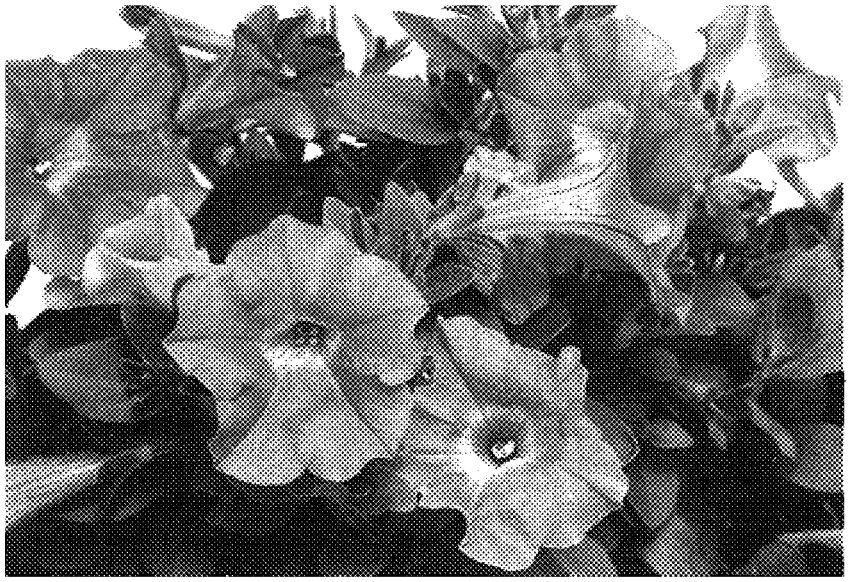
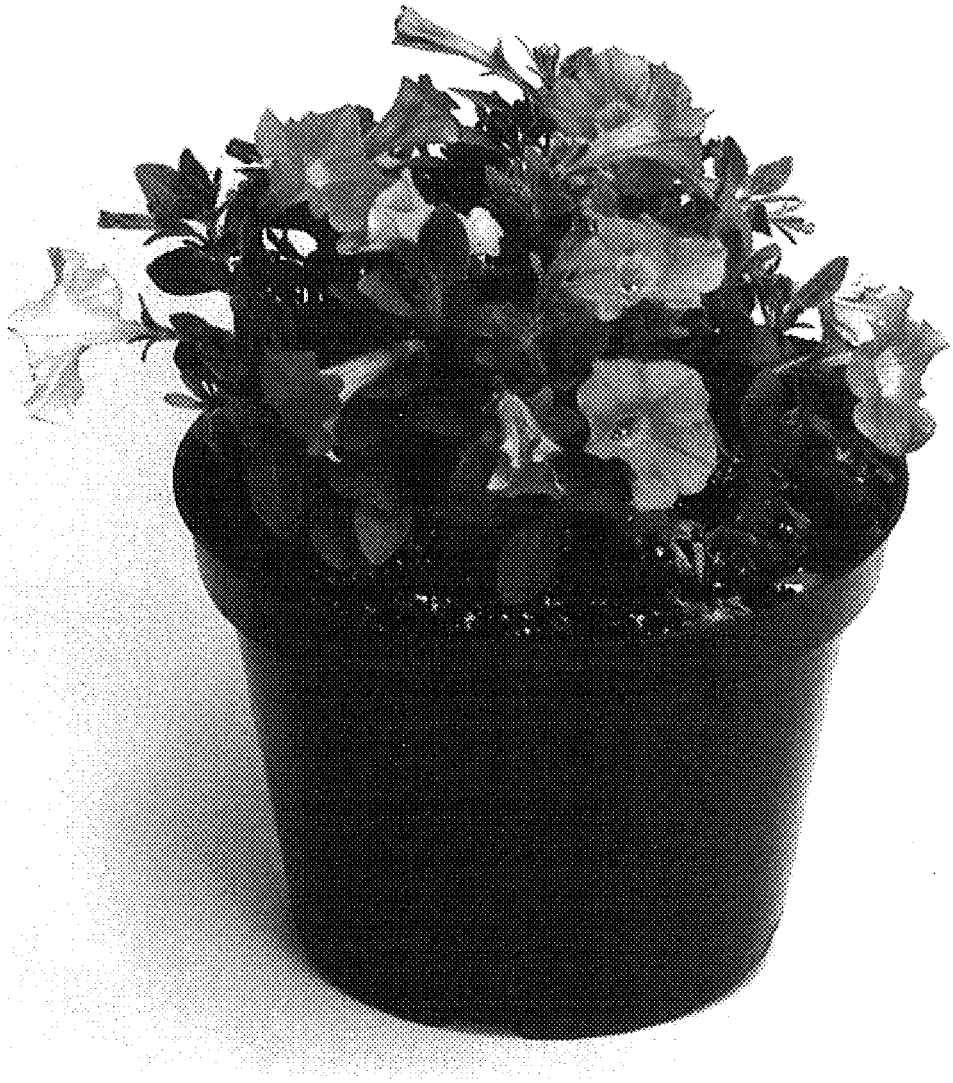

* * * * *